(12) United States Patent
Ataman et al.

(10) Patent No.: US 11,730,530 B2
(45) Date of Patent: Aug. 22, 2023

(54) DEVICE FOR TISSUE COAGULATION

(71) Applicant: Erbe Elektromedizin GmbH, Tuebingen (DE)

(72) Inventors: Caglar Ataman, Freiburg (DE); Klaus Fischer, Nagold (DE); Alexander Neugebauer, Moessingen (DE); Sergio Vilches, Freiburg (DE); Hans Zappe, Basel (CH)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 488 days.

(21) Appl. No.: 16/748,139

(22) Filed: Jan. 21, 2020

(65) Prior Publication Data

US 2020/0237421 A1 Jul. 30, 2020

(30) Foreign Application Priority Data

Jan. 24, 2019 (EP) .................... 19153586

(51) Int. Cl.
*A61B 18/04* (2006.01)
*A61B 18/00* (2006.01)

(52) U.S. Cl.
CPC .. *A61B 18/042* (2013.01); *A61B 2018/00577* (2013.01); *A61B 2018/00589* (2013.01);
(Continued)

(58) Field of Classification Search
CPC ........... A61B 2917/00791; A61B 2917/00648; A61B 2917/00589; A61B 2018/00648; A61B 18/042
See application file for complete search history.

(56) References Cited

U.S. PATENT DOCUMENTS 5,321,501 A 6/1994 Swanson et al.
5,608,520 A * 3/1997 Fleming ............... G01N 21/718
356/318

(Continued)

FOREIGN PATENT DOCUMENTS

BR 102016016596 A2 3/2017
CN 105592886 A 5/2016
(Continued)

OTHER PUBLICATIONS

European Decision to Grant dated Sep. 24, 2021, in corresponding European Application No. 19153586.3, with machine English translation (69 pages).

(Continued)

*Primary Examiner* — Linda C Dvorak
*Assistant Examiner* — Ryan T Clark
(74) *Attorney, Agent, or Firm* — Fitch, Even, Tabin & Flannery LLP

(57) ABSTRACT

The inventive device (10) can be used for tissue coagulation and/or tissue ablation. It comprises at least one electrode (16) that serves for generating a spark or plasma jet and is connectable to an electric source (20) for this purpose. The probe (11) is assigned to a measuring device (24) that emits and/or receives light in the proximity of the electrode (16) and determines the distance of the probe (11) from the tissue (36) and/or the tissue temperature and/or the composition of the influenced tissue (36). Preferably the measuring device (24) is operated synchronized with pulses or pauses of the pulse-pause-modulated radio frequency voltage ($U_{HF}$) of the electrode (16) in order to simultaneously carry out the desired measurements during the operation of the instrument (11) and to feedback control the operation of the instrument (11) based on the gained measurement results.

16 Claims, 4 Drawing Sheets

(52) U.S. Cl.
CPC .............. *A61B 2018/00648* (2013.01); *A61B 2018/00791* (2013.01)

(56) References Cited

U.S. PATENT DOCUMENTS

| | | | |
|---|---|---|---|
| 6,302,881 | B1 | 10/2001 | Farin |
| 7,720,532 | B2 | 5/2010 | Hashimshony et al. |
| 9,060,750 | B2 | 6/2015 | Lam |
| 2002/0026188 | A1* | 2/2002 | Balbierz ............ A61B 18/1206 606/41 |
| 2005/0010208 | A1 | 1/2005 | Winston et al. |
| 2006/0106371 | A1 | 5/2006 | Muhlhoff et al. |
| 2007/0213704 | A1 | 9/2007 | Truckai et al. |
| 2012/0289954 | A1 | 11/2012 | Lam |
| 2013/0199540 | A1* | 8/2013 | Buske ................ A61B 18/042 128/845 |
| 2014/0188092 | A1* | 7/2014 | Islam .................... A61B 18/22 606/15 |
| 2014/0188095 | A1* | 7/2014 | Weber ................... A61B 18/24 606/45 |
| 2014/0309632 | A1 | 10/2014 | Ogata et al. |
| 2014/0378961 | A1 | 12/2014 | Fischer et al. |
| 2017/0071652 | A1 | 3/2017 | Enderle et al. |

FOREIGN PATENT DOCUMENTS

| | | |
|---|---|---|
| CN | 106510842 A | 3/2017 |
| CN | 106794043 A | 5/2017 |
| CN | 110720979 A | 1/2020 |
| DE | 19860689 A1 | 8/2000 |
| DE | 19860689 C2 | 7/2001 |
| DE | 10323422 A1 | 4/2004 |
| DE | 10392791 T5 | 5/2005 |
| EP | 0868884 A2 | 10/1998 |
| EP | 2815695 A1 | 12/2014 |
| RU | 2126986 C1 | 2/1999 |
| RU | 2217035 C1 | 11/2003 |
| RU | 2384955 C1 | 3/2010 |
| RU | 2445041 C2 | 3/2012 |
| RU | 2464926 C2 | 10/2012 |
| RU | 2510248 C2 | 3/2014 |
| RU | 2620357 C2 | 5/2017 |
| RU | 2667319 C2 | 9/2018 |
| WO | 2010/104752 A2 | 9/2010 |
| WO | 2011055368 A2 | 5/2011 |
| WO | 2012/099974 A2 | 7/2012 |
| WO | 2013/164109 A1 | 11/2013 |
| WO | 2014145146 A1 | 9/2014 |

OTHER PUBLICATIONS

European Search Report and Written Opinion dated Jul. 16, 2019, in corresponding European Application No. 19153586.3, with machine English translation (10 pages).
Chinese First Office Action for CN Application No. 202010074139.6 dated Nov. 3, 2022, 6 pages.
Intellectual Property India Examination Report for Application No. 202014002246, dated Nov. 18, 2022; 6 pages.
National Intellectual Property Administration, P. R. China, Notification to Grant Patent Right for Invention for corresponding Chinese Patent Application No. 202010074139.6, dated May 26, 2023, 7 pages.
Federal Service for Intellectual Property; Office Action for corresponding Russian Patent Application No. 2020 101 946; dated May 30, 2023, 14 pages.
Federal Service for Intellectual Property; Search Report for corresponding Russian Patent Application No. 2020 101 946; dated May 30, 2023, 2 pages.

* cited by examiner

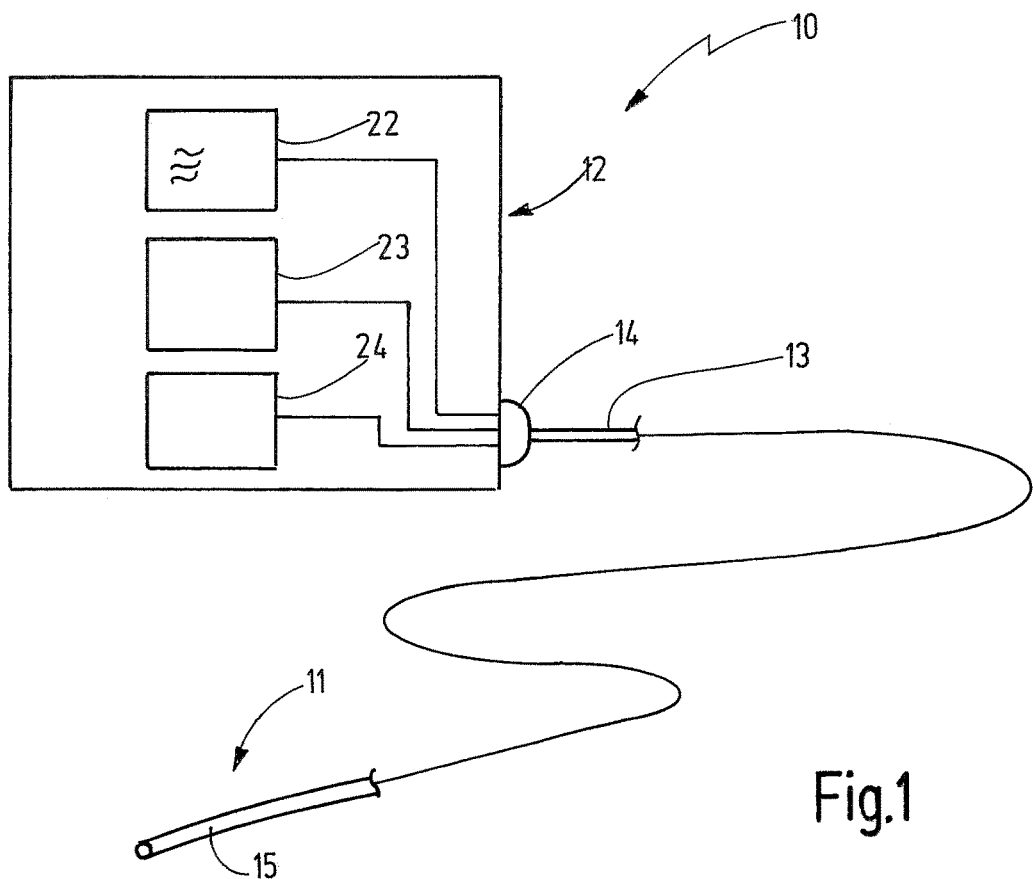
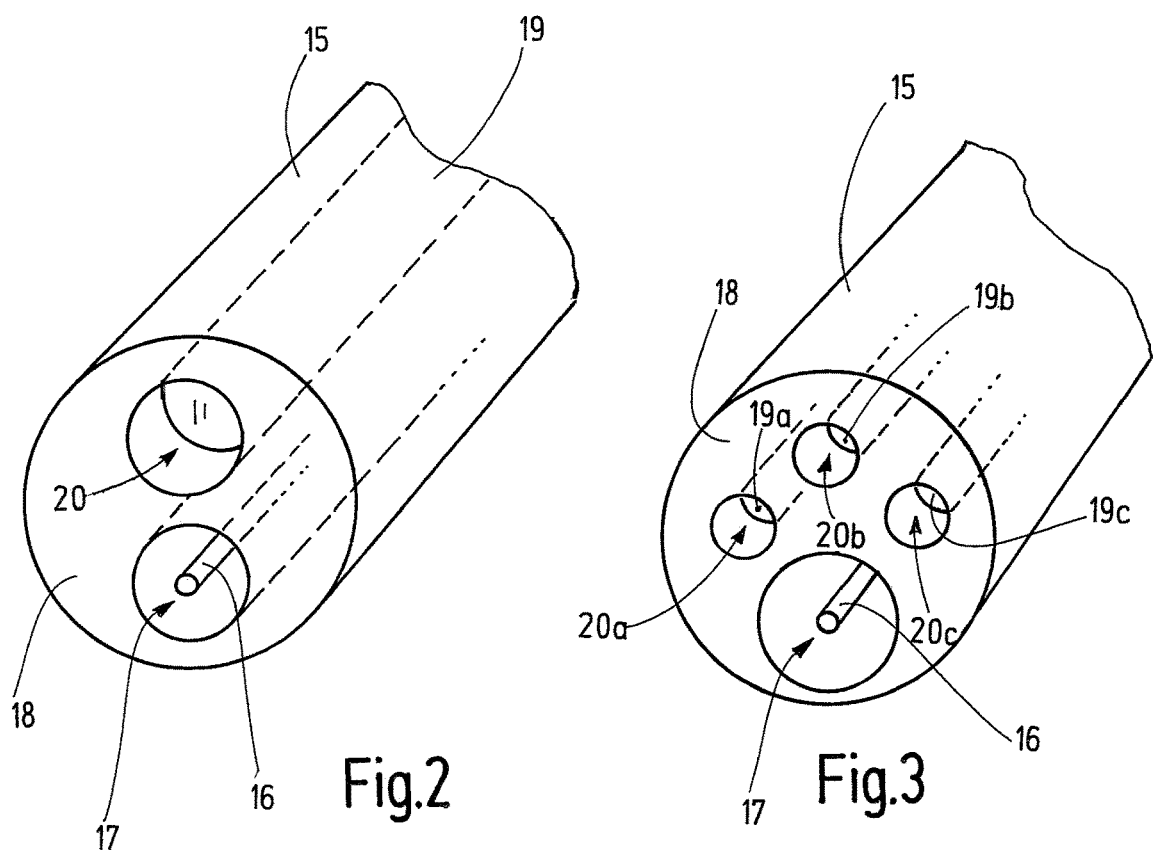
Fig.1
Fig.2
Fig.3

DEVICE FOR TISSUE COAGULATION

RELATED APPLICATION(S)

This application claims the benefit of European Patent Application No. 19153586.3, filed Jan. 24, 2019, the contents of which are incorporated herein by reference as if fully rewritten herein.

TECHNICAL FIELD

The invention refers to a device for the treatment of biological tissue. Instruments are known that influence tissue with electric energy, particularly for coagulation and ablation.

BACKGROUND

For example, WO 2012/099974 A2 discloses an instrument for this purpose that uses electromagnetic energy, e.g. in the form of a radio frequency current and voltage and an argon plasma for coagulation. Further this document refers to one or more sensors that can serve, e.g. to determine the power of the supplied energy, the effected depth, the tissue temperature or other physical parameters, e.g. a color. Further, electromyographic sensors for detection of the electromyography of the muscularis mucosa, a calorimetric sensor, a serum level sensor and an imaging sensor are mentioned.

US 2014/0309632 A1 describes a device having an instrument for tissue ablation by means of radio frequency energy, wherein for monitoring the ablation progress a respective measurement and monitoring system is provided. This system is configured to detect the tissue condition, which can be obtained by electric measurement at the treated tissue. As a possibility for measurement also intravascular ultrasonic measurement, optical coherence tomography, optical coherence reflectometry or angiography are mentioned.

U.S. Pat. No. 5,321,501 A describes an optical imaging of biological tissue by use of an interference optical sensor with which the tissue surface can be scanned. The probe can be an endoscope or angioscope and can be used for scanning a lumen. For parallel scanning a plurality of optical paths are provided. For increasing the focus, the focus point can be moved.

From WO 2010/104752 A2 an optical multi-function probe system for human and veterinary medical applications is known. The probe system uses the optical coherence tomography as measuring method and can execute a linear, two-dimensional or a depth-stepped scan of a tissue surface. Such scans are called A-scan, B-scan or C-scan. At least in one embodiment the probe can also be configured as radio frequency ablation probe.

Further a medical instrument for particularly precise ablation of biological tissue is known from US 2007/0213704 A1, wherein at least in one embodiment electrically applied electrodes are used for ablation that remove tissue by means of spark creation. Based on the light appearance due to the subsequent sparks, the tissue type can be determined with which the spark interacts. For evaluation a spectroscopic system is used to which the light emitted from the sparks is transmitted via an optical fiber. The analysis system determines the spectra of the light created by the sparks. By comparison of the obtained spectra with reference data it can be recognized if tissue is hit that shall remain unaffected, such that the ablation process can be stopped immediately.

U.S. Pat. No. 9,060,750 B2 describes a system with an instrument that influences a tissue by argon plasma coagulation. By means of optical emission spectroscopy that examines the received light, a conclusion is made on the presence of particular chemical substances.

U.S. Pat. No. 7,720,532 B2 describes an integrated instrument that can be used as versatile measuring instrument. It comprises an ultrasonic sensor comprising a plurality of ultrasonic transducers as well as an electric sensor with a central electrode and a ring-shaped electrode arranged in radial distance about the central electrode that are arranged together with the ultrasonic transducers at the distal front face of the instrument.

Additionally, US 2012/0289954 A1 discloses a plasma probe that can comprise one or more optical sensors that are provided for monitoring the ablation process. For controlling the ablation process the optical sensors can be connected with spectrometers that analyze the received light and based on this control the ablation process.

Starting therefrom it is the object of the invention to define a device that allows an improved process control.

SUMMARY

This object is solved with a device and a method as disclosed herein.

The inventive device can be used for tissue coagulation for example. A probe body that is part of the device comprises at least one electrode to which an electric voltage can be applied, preferably a radio frequency modulated or non-modulated voltage $U_{HF}$. An electric current is output from the electrode that flows through a plasma and over the biological tissue to be treated. The tissue is modified, particularly coagulated and/or removed.

At least one light conducting device is assigned to the probe body, wherein the at least one light conducting device is connected with a measuring device. The measuring device is configured as optical distance measuring device, as temperature measuring device or as tissue type determination device. It can also assume two or three or all of these functions as well as additional functions, if desired. Preferably the measuring device is configured as interferometric distance measuring device that works with multicolor light and allows an absolute distance determination. Short coherent light with a coherence length that is shorter than the desired distance between the probe and the tissue can be used as light, particularly white light. Also long coherence light with a coherence length that is larger than the desired distance between the probe and the tissue can be used as light.

The light conducting device comprises a light receiving window that defines an observation area. This observation area overlaps at least partly with the plasma jet or sparks output from the probe body.

The light receiving window can be formed at a GRIN-lens or at a lens array that preferably defines a plurality of optical axes and/or a plurality of focal points. In pairs the optical axes include an acute angle, i.e. an angle of at most 90°. They can also be orientated parallel with each other. Preferably the GRIN-lens or the lens array is connected with a monofilament light conducting device that in turn is connected with an optical measuring device.

If the optical measuring device serves for distance measurement, light can be supplied via the optical conductor to (all) optical axes and focal points and light scattered back therefrom is supplied via the light conducting device to the measuring device. This measuring device receives the light scattered back from different impact locations of the light of the different optical axes and creates an interference with the light of the light source. From the obtained interference pattern the distances between the tissue and the probe at the individual optical axes can be determined. Even though the determined distances cannot be assigned individually to individual focal points or optical axes, the measuring device can still be configured to determine the shortest measured distance (minimum distance) or also another desired value, like for example the average or the largest distance.

The distance measuring device is preferably an interferometric distance measuring device. It uses a light source with sufficient coherence length, at least one beam splitter, a light receiver, a light conductor and an objective lens. The objective lens can be a GRIN-lens; the beam splitter can be a fiber coupler; the light conductors can be optical fibers; the light receiver can be a photo diode or a photo diode array, e.g. in the form of a camera chip. The light path defined by the light conductors and the at least one beam splitter can comprise a measuring path and a reference path. The same optical elements, particularly the objective lens that is preferably configured as GRIN-lens, as well as the portion of the light path (e.g. the light conductor) leading from the beam splitter to the objective lens can form part of the reference path and the measuring path. The end surface of the objective lens (e.g. the GRIN-lens) that faces the tissue can serve as reference mirror.

The device can be configured such that the operation of the probe, particularly the activation of the electrode and of an potential plasma jet output therefrom, depend on the observance of particular distances, particularly on not falling below of a minimum distance. Because the different optical axes of the GRIN-lens or the lens array hit the tissue to be treated at different locations it can thus be guaranteed based on the plurality of impact locations that the biological tissue does not come too close to the probe at any location.

The inventive probe can particularly be used for a surgery robot. The distance measuring device facilitates this purpose remarkably. The distance between the probe and the tissue can be adjusted much simpler based on the distance measurement than based on camera image. In doing so, a remote control of the probe or also a semi-automatic or a fully automatic probe control is possible.

A probe can also comprise one or more electrodes. The probe can be integrated to a double probe with another similarly configured or structurally identical probe as well. The light conducting device can be provided inside the probe body, on the probe body or also on a holder that accommodates one or more probe bodies, for example. According to this principle, different probe configurations can be created that are adapted to different types of application or application locations.

If the measuring device is an interferometric distance measuring device, the light conducting device is concurrently configured for illuminating the measuring location, as well as also for conducting the light back to the measuring device that is scattered back from the measuring location. In doing so, the measuring device is preferably configured such that it is activated during pauses in which no light is emitted from the electrode and particularly from the spark or plasma originating from the electrode. If the electrode is, for example, supplied with a pulsed radio frequency voltage $U_{HF}$, the interferometric measuring device is preferably active in the pulse pauses of the radio frequency voltage $U_{HF}$.

The measuring device can also be used as pyrometric temperature measuring device. In this case it is configured to receive the light originating from the treated tissue, particularly infrared light, and to determine the temperature of the tissue based on the spectral composition of the received light. In this case the measuring device is preferably configured to be activated in pulse pauses of a pulsed radio frequency voltage $U_{HF}$ that is applied to the electrode.

The measuring device can also be a combined measuring device that performs an interferometric distance measurement as well as a pyrometric temperature measurement.

The measuring device can additionally or exclusively be configured to determine the tissue type to which the plasma or spark is emitted by means of optical emission spectroscopy. For this the measuring device is preferably configured to receive and to analyze light during the pulses of the pulsed treatment voltage (radio frequency voltage $U_{HF}$). The analysis of the light is preferably a spectral analysis in the context of which the light emitted from the spark or plasma is subject to a spectral examination. For the tissue distinction the measured spectra can be compared with reference spectra of particular tissue types. Particularly also spectral lines of chemical elements that are typical for particular tissue layers can be used as indicator for tissue layers, e.g. the spectral lines of magnesium or calcium. In the optical emission spectroscopy ES the intensity of the light signal is highly dependent from the distance. The consideration of this circumstance during the evaluation of the light signal allows a remarkable improvement in the evaluation of the emission spectra, particularly with reference to its comparison with pre-defined spectra. If the optical measuring device is configured to allocate the measured distance with the light signal, e.g. to calculate it based on the distance at which the comparison spectrum was detected, the interfering influence of varying distances during the treatment disappears. It is thus advantageous, if the optical measuring device is configured such that it considers the spectrum as well as the distance for the tissue type determination.

The measuring device can also be configured to be permanently active in order to determine the distance of the probe from the tissue and/or the temperature of the tissue during the pulse pauses and to determine the tissue composition during the pulses.

A part of the invention is also a method for tissue ablation, in which the ablation progress and/or the distance of the probe body from the surface of the biological tissue and/or the tissue type is determined by means of the optical measuring device. The method is particularly suitable for mucosa ablation. During the plasma-assisted ablation of the gastric mucosa of patients layer-specific emission spectra (ES) can be detected and accordingly the respective treated tissue layers can be indicated or otherwise signalized to the surgeon. The advancing of the ablating plasma in the sub-mucosa layer can be detected by an increase of at least one ES-signal of magnesium compared with the mucosa layer and can be indicated. The advancing of the ablating plasma in the sub-mucosa layer can also be detected by an increase of at least one ES-signal of calcium compared with the mucosa layer and can be indicated. Also a coincidence of the increase of the ES-signals of magnesium with the increase of the ES-signals of calcium or another marker as indicator for the advancing of the plasma in the sub-mucosa can be used.

Particularly the advancing of the ablating plasma in the muscularis propria (muscle layer) can be detected by an increase of at least one ES-signal of magnesium compared with the mucosa layer and can be indicated.

Also the advancing of the ablating plasma in the muscularis propria (muscle layer) can be detected by an increase of at least one ES-signal of calcium or of another marker compared with the mucosa layer can be detected and indicated.

BRIEF DESCRIPTION OF THE DRAWINGS

Further details of embodiments of the invention are subject matter of dependent claims as well as the drawings and the specification. The drawings show:

FIG. 1 illustrates an inventive device in a schematic overview,

FIGS. 2-4 illustrate different embodiments of probes for tissue ablation in perspective sectional illustration.

DETAILED DESCRIPTION

Figure 4:
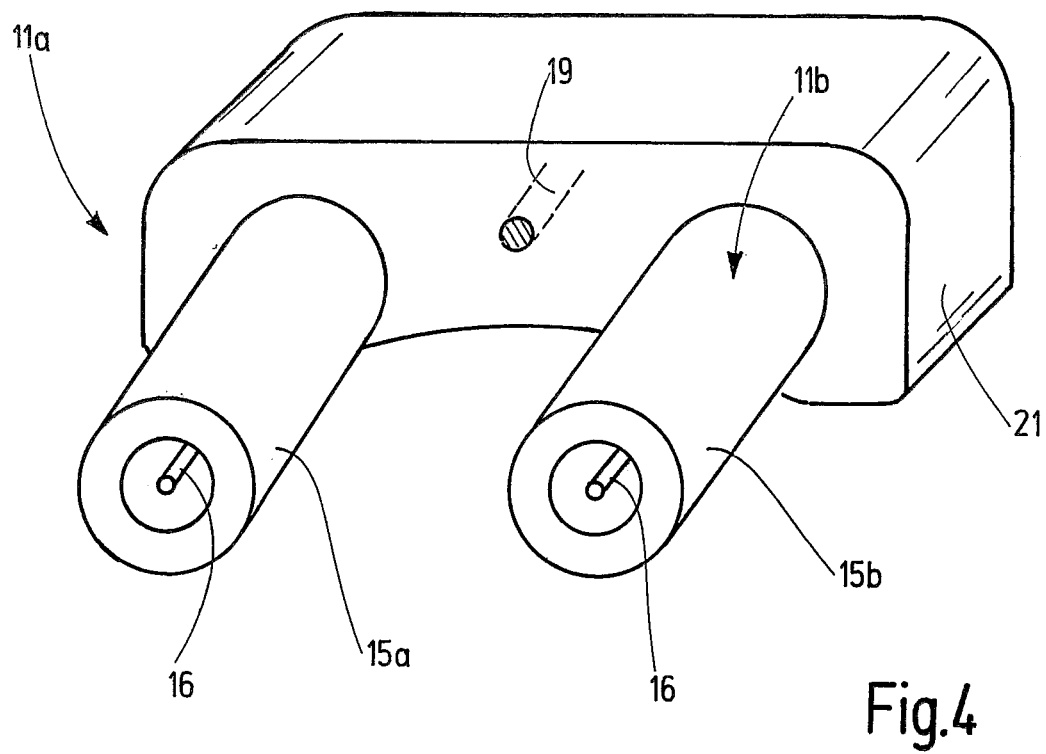

FIG. 1 illustrates a device 10 that can be used for tissue coagulation, for tissue ablation or other tissue treatment. A probe 11 and a supply device 12 supplying the probe 11 form part of the device 10. The supply device 12 can be formed by one or more apparatus and is illustrated in FIG. 1 simplified as a block. The subsequent use of the term "device 12" also comprises a plurality of operatively integrated or coupled apparatus.

The probe 11 can be a probe for endoscopic use or also an instrument for laparoscopic use or for the open surgery use. The structural and functional details explained subsequently apply for each of these configurations, unless it is not excluded in principle.

The probe 11 is connected with the device 12 via one or more conductors 13 as well as one or more connectors 14, wherein the device 12 provides the operation power and the media for the operation of the probe 11. The probe 11 comprises a rigid or flexible probe body 15 in or on which an electrode 16 is supported. In the present embodiment the electrode 16 is arranged in a fluid channel 17 that extends longitudinally through the probe body 15 and that leads to the connector 14 and through which an electric conductor extends that supplies the electrode 16 with electric power. The fluid channel 17 preferably opens out at a front face 18 of the distal end of the probe body 15. The probe body 15 can be further provided with a light conducting device 19 that extends from the distal end of the probe body 15 to the connector 14. At the distal end of the light conducting device 19 an opening 20 is provided through which light can enter and exist and thus can be emitted from the light conducting device 19 to a treatment location and can be received therefrom. Preferably the fluid channel 17 and the light conducting device 19 extend in the same direction through the probe body 15.

As it can be seen in FIG. 3, it is also possible to provide several light conducting devices 19a, 19b, 19c that extend through the probe body 15 and lead to the connector 14.

Then also several windows 20a, 20b, 20c can be provided at the front face 18 accordingly.

FIG. 4 illustrates a further modification, in which two probes 11a, 11b are integrated into one twin probe. The two probes 11a, 11b can be configured similarly or differently. They can be formed with or without optical light conducting device as well as with or without light entry window or light exit window. In the example shown in FIG. 4, a light conducting device 19 is attached to a holder 21 that connects the two probes 11a, 11b with each other. The presented special variations of FIGS. 2-4 are examples that can be combined with each other. For example the probes according to FIGS. 2 and 3 can be integrated with a holder of FIG. 4 to form a twin probe. Also one of the probes according to FIG. 2 or 3 can be integrated with one of the probes 15a or 15b in the holder 21 of FIG. 4 to form a twin probe. All of these arrangements have in common that they comprise at least one electrode 16, at least one light conductor 19 and at least one fluid channel 17. Accordingly, in the device 12 at least one electric generator 22 that is connected via the connector 14 and the conductor 13 with the electrode 16, a gas source 23 that is connected via the connector 14 and the conductor 13 with the fluid channel 17 and a measuring device 24 that is connected via the connector 14 and the conductor 13 with the light conducting device 19, are provided.

Figure 10:
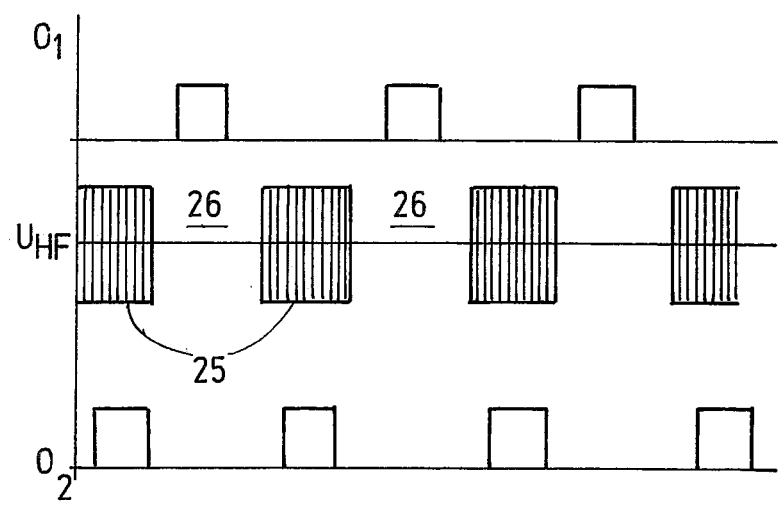

The generator 22 is preferably a controllable radio frequency generator that is controlled by a not further illustrated control circuit. It is preferably configured to output a high frequency alternating voltage $U_{HF}$ preferably with a frequency of clearly over 100 kHz, e.g. 350 kHz. It is further configured to modulate the radio frequency alternating voltage $U_{HF}$, e.g. with a square wave, such that a pulsed voltage output with pulses 25 and pauses 26 is obtained as it is shown in FIG. 10 for the radio frequency alternating voltage $U_{HF}$. The control or the generator 22 respectively can be configured to vary the ratio of the durations of the pulses 25 and the pauses 26 according to pre-defined adjustments, pre-defined modes or according to control signals as well.

The gas source 23 can also be connected with a not further illustrated control device in order to selectively release or block a gas flow and/or to adjust the flow rate. The blocking and releasing of the gas flow and/or the adjustment of the flow rate can be carried out according to user adjustments, according to selected operating modes and/or based on control signals.

The measuring device 24 is an optical measuring device that can be configured as optical distance measuring device and/or as pyrometric temperature measuring device and/or measuring device for determination of a tissue type, preferably based on the optical emission spectroscopy. If the optical measuring device 24 determines a plurality of parameters concurrently, e.g. distance and temperature or distance and tissue type, improved accuracies for the temperature or the tissue type can be obtained as without consideration of the distance.

Figure 5:
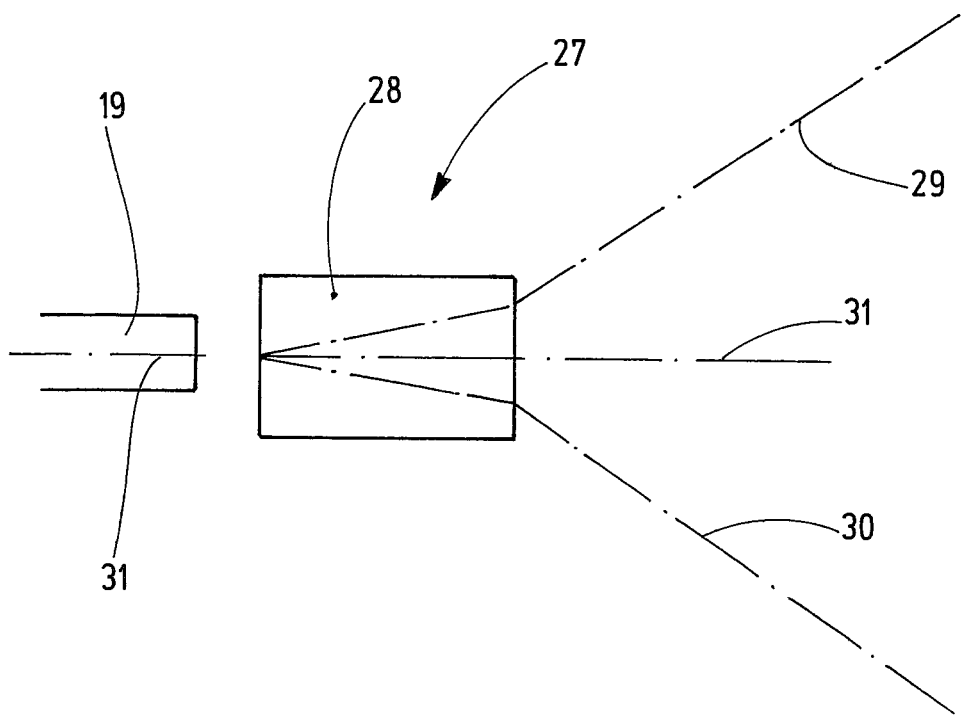
FIG. 5 shows a schematic illustration of a distal end of a light conducting device and a GRIN-lens by its different optical axes that cooperates with the light conducting device, FIG. 6 the GRIN-lens of FIG. 5 and the light bundles defined by the GRIN-lens, FIG. 7 an interferometer device in a schematic illustration, FIG. 8 an interferometric spectrum created by the interferometer and the measured distances derived therefrom, FIG. 9 the cooperation of components of the device of FIG. 1 in individual isolated schematic illustration, and FIG. 10 diagrams for illustrating the principle of the operation of the device according to FIG. 1 or 9 respectively.

At the distal end of the light conducting device 19 the lens arrangement 27 can be arranged serving as objective lens that comprises a GRIN-lens 28, e.g. as schematically illustrated in FIG. 5. It can be configured such that the beam path is divided or split in several optical axes 29, 30, 31. A central optical axis 31 can be identical with the optical axis 31 of the light conducting device 19. Additional optical axes 29, 30 can be arranged on the envelope of a cone around the optical axis 31 (e.g. a number of 6). In pairs the optical axes 29, 30, 31 can include an angle, preferably an angle of at most 90°, i.e. an acute angle.

Figure 6:
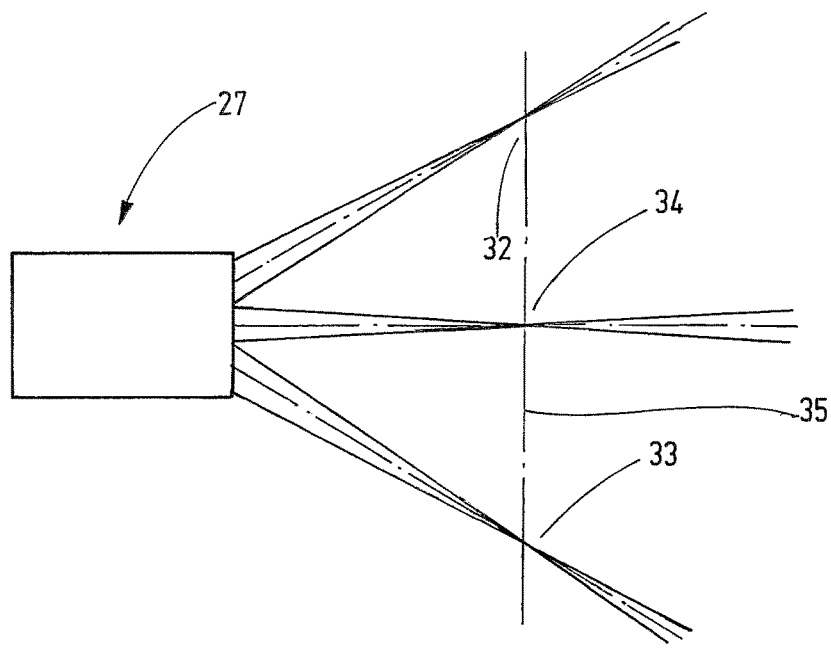

FIG. 6 illustrates light bundles that are obtained for the lens arrangement 27 of FIG. 5 that can be focussed and can thus define focal points 32, 33, 34. These focal points are preferably arranged on a common area 35, e.g. a sphere, a cylinder surface or a plane. Additionally, they are preferably arranged at a distance from the GRIN-lens 28 that is substantially equal to the distance in which the GRIN-lens 28 is located away from the biological tissue 36 during use of the probe 15, as it is schematically indicated in FIG. 7.

Figure 7:
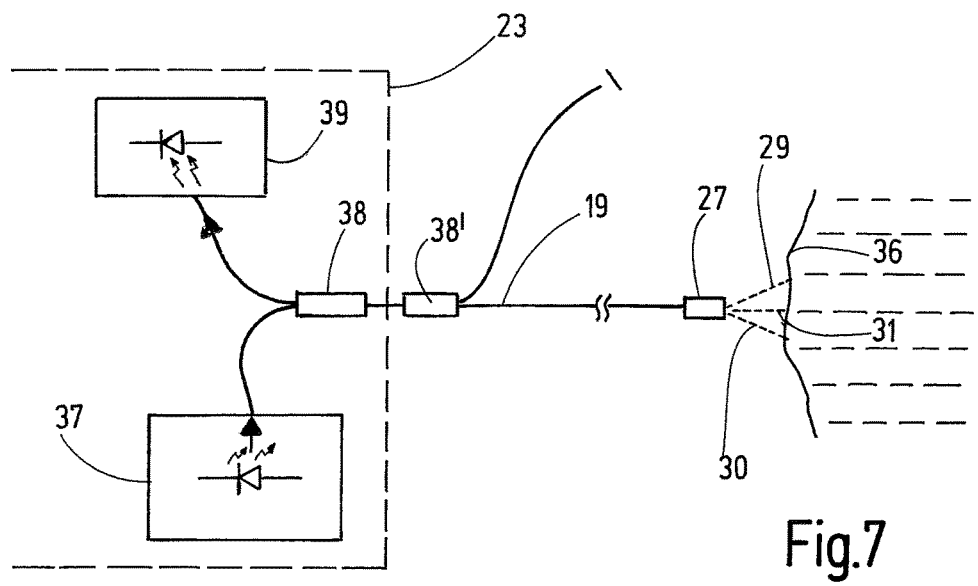

FIG. 7 illustrates schematically and mainly limited to the optical components the structure of the measuring device 24 that is configured as interferometric measuring device for distance control or distance measurement. A light source 37, e.g. in form of a white light source or a tunable laser, is part of the measuring device. It is connected with the light conducting device 19 by a fiber coupler 38 that serves as beam splitter. The fiber coupler 38 is further connected with a light receiver 39 that receives portions of the light emitted from the light source 37 as well as portions of the light reflected at the surface of the tissue 36. As necessary a reference light path terminated with a reflector can be coupled with the beam path via a further fiber coupler 38'. However, in a preferred embodiment the light path in the section of the light conducting device 19 from the beam splitter 38 to the GRIN-lens until the end face thereof serves as reference light path. The end face of the GRIN-lens (or of another objective lens) reflects a portion of the light and thus forms a reference mirror. A separate reference light path can be omitted.

Figure 8:
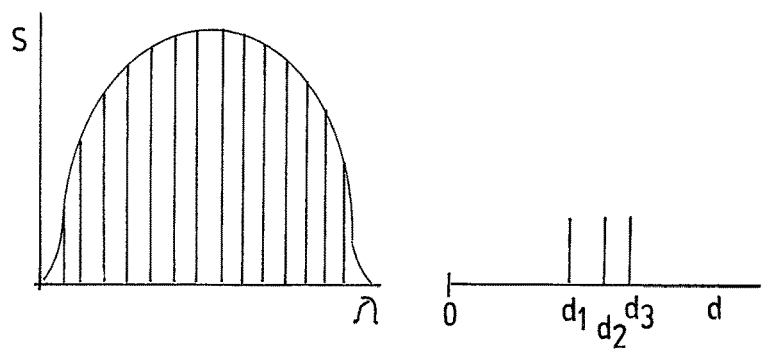

Depending on the wavelength $\lambda$, constructive and destructive interference is obtained at the light receiver 39, such that the light receiver 39 receives a light spectrum S, as it is shown on the left side in FIG. 8.

The interferometer can be configured to operate with short coherent light (white light interferometer) as well as with light of longer coherence length.

In the present embodiment a tunable light source 37 is used for distance measurement in the measuring device 24 that is able to emit light with variable wavelength. The individual spectral lines of the light spectrum are subsequently received during tuning of the light source 37. If, on the contrary, a light source 37 is used that emits several or all colors concurrently, the spectrum of FIG. 8 can be created by spectral decomposition of the light supplied from the fiber coupler 38 to the light receiver 39 and can be registered and created by a respective plurality of light-receiving elements.

The spectrum shown on the left side of FIG. 8 has been created by interference of light emitted from the light source 37 with light of the different impact locations, at which the optical axes 29, 30, 31 intersect the surface of the biological tissue 36. In so far it is a sum spectrum. Therefrom the individual distance values $d_1$, $d_2$, $d_3$ of the intersection locations of the optical axes 29, 30, 31 with the surface of the tissue 36 from the GRIN-lens 28 can be determined. Additionally, other not illustrated distances are measured created by reflections that occur at deeper tissue layers. This particularly applies for operations on transparent tissue layers.

The measuring device 24 can be configured to determine the smallest of the distance values $d_1$, $d_2$, $d_3$ and to provide this value to the control of the device 12 for the further processing. The control can control the generator 22 based on this value, e.g. switch the generator on and off or influence the power and/or the duty cycle (pulse-pause-ratio) of the generator. The control can also switch the gas source 23 on and off or initiate an increased or decreased gas output based on this smallest distance value $d_1$.

Figure 9:
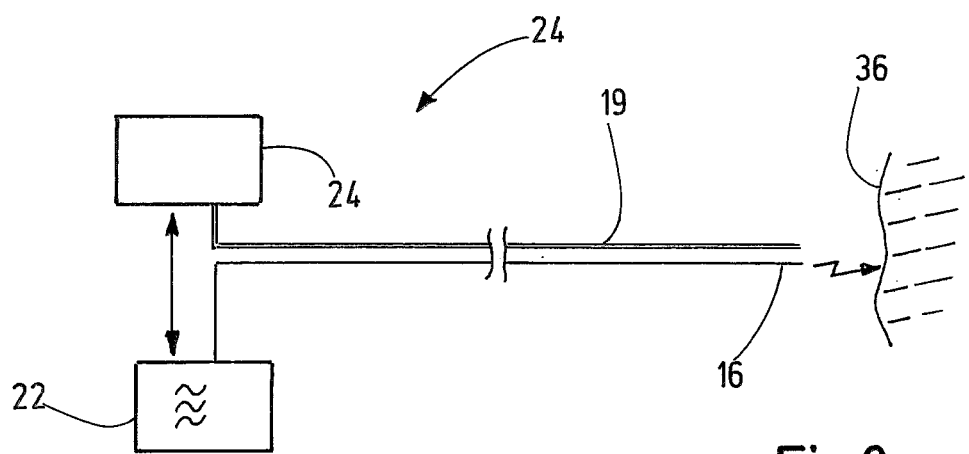

Preferably the interference-optically operating measuring device 24 described so far is active during pauses 26 of the pulsed radio frequency voltage $U_{HF}$ applied to the electrode 16, as it is illustrated in FIG. 10 in the top diagram for the first optical measurement $O_1$. For this the generator 22 can communicate directly or via a control of the device 12 with the optical measuring device 24, as schematically illustrated in FIG. 9, such that the measuring device 24 operates synchronized with the generator 22.

It is also possible to configure the measuring device 24, such that it carries out a tissue surface temperature measurement additionally or alternatively by detecting, also during the pauses 26, the radiation originating from the surface of the tissue 36, particularly infrared radiation, and carries out a pyrometric temperature detection based thereon.

Alternatively or additionally it is also possible to use the optical measuring device 24 as part of a tissue determination or tissue classification device that determines the type of the tissue hit by the spark or the plasma by optical emission spectroscopy. The measurement is illustrated in the lower diagram $O_2$ in FIG. 10. Apparently the measuring device 24 for executing the measurement is preferably active during the pulses 25. For this the light source 37 is inactive or totally omitted. In the latter case the fiber coupler 38 (and, if present, also the fiber coupler 38') can also be omitted. The light receiver 39 receives the light originated from the spark or the plasma and determines in turn the spectrum thereof according to the illustration on the left side in FIG. 8. The detected spectrum can be compared with a reference spectrum in order to conclude on the tissue type therefrom. For determination of the tissue type, particularly for distinction of the mucosa, sub-mucosa and muscularis propria (muscle layer) in the mucosa ablation, e.g. for reducing or eliminating of ghrelin cells, also the typical spectral lines of magnesium and/or calcium can be detected from the presence and dimension of which it can be determined with which layer the plasma interacts, i.e. which layer is ablated.

The measuring device 24 can create one more control signals accordingly that characterize the smallest distance between the probe and the tissue and/or the tissue temperature and/or the tissue type. The control device of the device 12 can be configured to control the generator 22 and/or the gas source 23 according to these signals. For example, the control device can stop the generator 22 as soon as a minimum distance of the probe from the tissue is undercut. Simultaneously or shortly after, the control device can deactivate the gas source 23. Alternatively the probe can be automatically guided at least with reference to its distance from the tissue, in that a distance control device automatically adjusts the desired treatment distance between the probe and the tissue based on the distance measurement. It is also possible to indicate the measured distance during the operation of the probe to a surgeon, such that he must not only rely on a camera image during the guidance of the probe. In combination with any of the above-mentioned variations or independent therefrom, it is also possible to adapt the energy supply, current amount, voltage, modulation or any other characteristic of the electric power supplied from the generator dependent on the distance, i.e. to adjust the electric power dependent on the measured distance, such that the tissue effect does not or not remarkably change due to the change in distance.

Additionally or alternatively the control device can deactivate the generator 22 and/or the gas source 23 as soon as the measuring device 24 determines the influence of a tissue type based on the emission spectrum of plasma or the spark that shall not be influenced. The cooperation of the measuring device 24 with, e.g. the generator 22 is schematically illustrated in FIG. 9. In doing so, it can go beyond the switching on and switching off of the generator 22 and/or the gas source 23. For example, the pulse-pause-ratio of the generator 22 and/or the amount of the gas flow of the gas source 23 can be adjusted or feedback controlled based on the control signal. For example, the pulse-pause-ratio of the radio frequency voltage $U_{HF}$ output from the radio frequency generator 24 can be decreased, if the tissue temperature measured by the measuring device exceeds a limit value. Concurrently the gas flow of the gas source 23 can be increased or also decreased. In doing so, an automatic adaption of the operation of the generator 22 and/or the gas source 23 at the respective temporary operating conditions of the probe 11 can be achieved.

In all embodiments of the inventive device 10 that is useable for tissue coagulation or tissue ablation, an electrode 16 to which a radio frequency voltage is applied and a light conducting device 19 can be provided at a probe body that can form part of a medical instrument, wherein the light conducting device 19 is connected with a measuring device 24. This measuring device 24 can be configured as optical distance measuring device and/or as temperature measuring device as well as at least optionally also as device for determination of the treated tissue type by optical emission spectroscopy. As far as the optical measuring device serves as distance measuring device, it is particularly preferably configured as interference optical measuring device that is configured to concurrently determine the distance of the probe or the light conducting device from a plurality of points of the treated tissue. In doing so, it is possible to detect the minimum distance of the probe over a tissue area in which individual measuring points of the optical measuring device are distributed and to control the operation of the probe dependent therefrom. As a consequence, the peak voltage, power, the pulse-pause-ratio or other electrical characteristics of the used radio frequency voltage $U_{HF}$ applied to the electrode or the gas flow can be modified or also simply the switching off of the radio frequency generator and the gas flow can be carried out.

The inventive device 10 can be used for tissue coagulation and/or tissue ablation. It comprises at least one electrode 16 that serves for generating a spark or plasma jet and is connectable to an electric source 20 for this purpose. The probe 11 is assigned to a measuring device 24 that emits and/or receives light in the proximity of the electrode 16 and determines the distance of the probe 11 from the tissue 36 and/or the tissue temperature and/or the composition of the influenced tissue 36. Preferably the measuring device 24 is operated synchronized with pulses or pauses of the pulse-pause-modulated radio frequency voltage $U_{HF}$ of the electrode 16 in order to simultaneously carry out the desired measurements during the operation of the instrument 11 and to feedback control the operation of the instrument 11 based on the gained measurement results.

LIST OF REFERENCE SIGNS 10 device for ablation or coagulation of tissue
11 probe 11a, 11b
12 supply device/apparatus
13 conductor
14 connector
15 probe body 15a, 15b
16 electrode
17 fluid channel
18 front face
19 light conducting device 19a, 19b, 19c
20 window 20a, 20b, 20c
21 holder
22 generator
23 gas source
24 optical measuring device
25 pulse
26 pause
27 lens
28 GRIN-lens
29-31 optical axes
32-34 focal points
35 area
36 biological tissue
37 light source
38 fiber coupler
39 light receiver

The invention claimed is:

1. A device (10), particularly for tissue coagulation, comprising:
a probe (11) having a probe body (15) comprising at least one fluid channel (17) configured to be connected to a gas source,
at least one electrode (16) arranged in the at least one fluid channel (17), to which an electric voltage ($U_{HF}$) can be applied for creating a plasma in a space between a tissue to be treated and the at least one electrode (16) from a gas supplied by the gas source such that an electric current output from the at least one electrode (16) flows through the space via the plasma into the tissue,
an optical measuring device (24), and
at least one light conducting device (19) that is assigned to the probe body (15) and that is configured to be connected to the optical measuring device (24),
wherein the optical measuring device (24) comprises an optical interferometric distance measuring device configured to determine the distance of the probe from the tissue.

2. The device according to claim 1, wherein a GRIN-lens (28) or a lens array that defines a plurality of focal points (32, 33, 34), is arranged at a distal end of the at least one light conducting device (19).

3. The device according to claim 2, wherein the plurality of focal points (32, 33, 34) are arranged on a plane (35).

4. The device according to claim 2, wherein the GRIN-lens (28) or lens array is configured to define at least one optical axis (29, 30, 31) which is parallel or defines an acute angle with the at least one electrode (16).

5. The device according to claim 4, wherein the at least one optical axis is a plurality of different optical axes (29, 30, 31) and the optical measuring device (24) is configured as a distance measuring device and is configured to indicate a shortest distance determined along the plurality of different optical axes (29, 30, 31).

6. The device according to claim 1, wherein the probe body (15) comprises at least two electrodes (16) including the at least one electrode.

7. The device according to claim 1, wherein a light source (37) is provided for the interferometric distance measurement that is configured to emit light of different wavelengths ($\lambda$) simultaneously or at different points of time.

8. The device according to claim 1, wherein the optical measuring device (24) comprises a pyrometer that serves as a temperature measuring device.

9. The device according to claim 1, wherein the optical measuring device (24) comprises an optical emission spectrometer that serves as a tissue type determination device.

10. The device according to claim 1, wherein the optical measuring device (24) comprises a combination of at least one photo diode with at least one optical filter.

11. The device according to claim 1, wherein the probe body (15), the at least one electrode (16) and the at least one light conducting device (19) are configured as part of an instrument (15) for tissue treatment and the optical measuring device (24) is configured as part of a supply device (12) for supply of the instrument.

12. The device according to claim 11, wherein the supply device (12) comprises a generator (22) for creating a radio frequency pulsed voltage (UHF) with pulses (25) and pulse pauses (26) to which the at least one electrode (16) of the instrument (15) is configured to be connected, wherein the optical measuring device (24) is active at least during the pulse pauses (26).

13. The device according to claim 11, wherein the supply device (12) comprises a generator (22) and a control device; wherein the control device is configured to adjust a flow rate of the gas and to control the generator (22) and/or the gas source (23) depending on signals created by the optical measuring device (24) characterizing at least one of:
a smallest distance between the probe (11) and the tissue;
a temperature of the tissue; and
a type of the tissue.

14. The device according to claim 13, wherein the control device is configured to deactivate the generator (22) when the smallest distance between the probe (11) and the tissue is less than or equal to a predetermined minimum distance.

15. The device according to claim 13, wherein the control device is configured to adapt at least one characteristic parameter of an electric power supplied by the generator (22) depending on the smallest distance between the probe (11) and the tissue.

16. The device according to claim 13, wherein the control device is configured to deactivate the generator (22) and/or the gas source (23) when the optical measuring device (24) determines a predetermined tissue type has been influenced based on an emission spectrum of the plasma detected by the optical measuring device (24).

* * * * *